(12) United States Patent
Epenetos et al.

(10) Patent No.: US 9,145,446 B2
(45) Date of Patent: Sep. 29, 2015

(54) CONJUGATE COMPRISING P21 PROTEIN FOR THE TREATMENT OF CANCER

(75) Inventors: Agamemnon Epenetos, London (GB); Christina Kousparou, London (GB)

(73) Assignee: Trojan Technologies, Ltd., London (GB)

( * ) Notice: Subject to any disclaimer, the term of this patent is extended or adjusted under 35 U.S.C. 154(b) by 694 days.

(21) Appl. No.: 12/608,718

(22) Filed: Oct. 29, 2009

(65) Prior Publication Data
US 2011/0021441 A1    Jan. 27, 2011

Related U.S. Application Data

(63) Continuation of application No. 11/911,427, filed as application No. PCT/GB2006/001407 on Apr. 18, 2006, now abandoned.

(30) Foreign Application Priority Data

Apr. 14, 2005 (GB) ................................. 0507598.1

(51) Int. Cl.
| | |
|---|---|
| *A61K 6/00* | (2006.01) |
| *A61K 38/00* | (2006.01) |
| *A61K 38/16* | (2006.01) |
| *A61K 47/00* | (2006.01) |
| *A61K 47/30* | (2006.01) |
| *C07K 14/435* | (2006.01) |
| *A61K 31/337* | (2006.01) |
| *A61K 31/513* | (2006.01) |
| *A61K 31/555* | (2006.01) |
| *A61K 33/24* | (2006.01) |
| *A61K 38/17* | (2006.01) |
| *A61K 45/06* | (2006.01) |
| *C07K 14/47* | (2006.01) |
| *A61K 47/48* | (2006.01) |

(52) U.S. Cl.
CPC ......... *C07K 14/43581* (2013.01); *A61K 31/337* (2013.01); *A61K 31/513* (2013.01); *A61K 31/555* (2013.01); *A61K 33/24* (2013.01); *A61K 38/1709* (2013.01); *A61K 45/06* (2013.01); *A61K 47/48246* (2013.01); *C07K 14/4738* (2013.01); *C07K 2319/10* (2013.01)

(58) Field of Classification Search
CPC . A61K 2236/00; A61K 2300/00; A61K 6/00; A61K 38/00; A61K 38/16; A61K 47/00; A61K 47/30; A61K 47/48238; A61K 47/48246

See application file for complete search history.

(56) References Cited

U.S. PATENT DOCUMENTS

| | | | |
|---|---|---|---|
| 6,521,602 B1 | 2/2003 | Patel et al. | |
| 2002/0068706 A1 | 6/2002 | Gyuris et al. | |
| 2003/0133971 A1 | 7/2003 | Smith et al. | |
| 2003/0148265 A1* | 8/2003 | Brooks et al. ...................... 435/5 |
| 2004/0110928 A1* | 6/2004 | Crisanti et al. ................. 530/358 |

OTHER PUBLICATIONS

Children's Hospital Boston. "Cancer stem cells are not one size fits all,' lung cancer models show." ScienceDaily. ScienceDaily, Jul. 5, 2010.*

Ball, K.L. et al. "Cell-cycle arrest and inhibition of Cdk4 activity by small peptides based on the carboxy-terminal domain of p21$^{WAF1}$" *Current Biology*, 1996, 7:71-80.

Bonfanti, M. et al. "p21$^{WAF1}$—derived Peptides Linked to an International Peptide Inhibit Human Cancer Cell Growth" *Cancer Reseach*, Apr. 15, 1997, 57:1442-1446.

Hariton-Gaza, E. et al. "Direct translocation of histone molecules across cell membranes" *Journal of Cell Science*, 2003, 116(22):4577-4586.

Mutoh, M. et al, "A p21$^{Waf1/Clp1}$ Carboxyl-terminal Peptide Exhibited Cyclin-dependent Kinase-inhibitory Acvitity and Cytotoxicity When Introducced into Human Cells" *Cancer Research*, Jul. 15, 1999, 59:3480-3488.

Wadia, J.S. et al. "Transmembrane delivery of protein and peptide drugs by TAT-mediated transduction in the treatment of cancer" *Advanced Drug Delivery Reviews*, 2005, 57:579-596.

* cited by examiner

*Primary Examiner* — Alana Harris Dent
(74) *Attorney, Agent, or Firm* — DLA Piper LLP (US)

(57) ABSTRACT

The P21 protein is used as a medicament in the treatment of cancer. A conjugate comprises a first region comprising the P21 protein, or a homologue or functional fragment thereof; and a second region comprising a translocation factor.

6 Claims, 12 Drawing Sheets

SEQUENCE LISTING

```
<160> NUMBER OF SEQ ID NOS: 6

<210> SEQ ID NO 1
<211> LENGTH: 163
<212> TYPE: PRT
<213> ORGANISM: Homo sapiens

<400> SEQUENCE: 1

Ser Glu Pro Ala Gly Asp Val Arg Gln Asn Pro Cys Gly Ser Lys Ala
1               5                   10                  15

Cys Arg Arg Leu Phe Gly Pro Val Asp Ser Glu Gln Leu Ser Arg Asp
            20                  25                  30

Cys Asp Ala Leu Met Ala Gly Cys Ile Gln Glu Ala Arg Glu Arg Trp
        35                  40                  45

Asn Phe Asp Phe Val Thr Glu Thr Pro Leu Glu Gly Asp Phe Ala Trp
    50                  55                  60

Glu Arg Val Arg Gly Leu Gly Leu Pro Lys Leu Tyr Leu Pro Thr Gly
65                  70                  75                  80

Pro Arg Arg Gly Arg Asp Glu Leu Gly Gly Gly Arg Arg Pro Gly Thr
                85                  90                  95

Ser Pro Ala Leu Leu Gln Gly Thr Ala Glu Glu Asp His Val Asp Leu
            100                 105                 110

Ser Leu Ser Cys Thr Leu Val Pro Arg Ser Gly Glu Gln Ala Glu Gly
            115                 120                 125

Ser Pro Gly Gly Pro Gly Asp Ser Gln Gly Arg Lys Arg Arg Gln Thr
        130                 135                 140

Ser Met Thr Asp Phe Tyr His Ser Lys Arg Arg Leu Ile Phe Ser Lys
145                 150                 155                 160

Arg Lys Pro
```

```
<210> SEQ ID NO 2
<211> LENGTH: 9
<212> TYPE: PRT
<213> ORGANISM: Human immunodeficiency virus

<400> SEQUENCE: 2

Arg Lys Lys Arg Arg Gln Arg Arg Arg
1               5

<210> SEQ ID NO 3
<211> LENGTH: 60
<212> TYPE: PRT
<213> ORGANISM: Drosophila melanogaster

<400> SEQUENCE: 3

Arg Lys Arg Gly Arg Gln Thr Tyr Thr Arg Tyr Gln Thr Leu Glu Leu
1               5                   10                  15

Glu Lys Glu Phe His Phe Asn Arg Tyr Leu Thr Arg Arg Arg Arg Ile
                20                  25                  30

Glu Ile Ala His Ala Leu Cys Leu Thr Glu Arg Gln Ile Lys Ile Trp
            35                  40                  45

Phe Gln Asn Arg Arg Met Lys Trp Lys Lys Glu Asn
    50                  55                  60

<210> SEQ ID NO 4
<211> LENGTH: 16
<212> TYPE: PRT
<213> ORGANISM: Drosophila melanogaster

<400> SEQUENCE: 4

Arg Gln Ile Lys Ile Trp Phe Gln Asn Arg Arg Met Lys Trp Lys Lys
1               5                   10                  15

<210> SEQ ID NO 5
<211> LENGTH: 16
<212> TYPE: PRT
<213> ORGANISM: Artificial
<220> FEATURE:
<223> OTHER INFORMATION: pAntp Helix 3 Variant; between 6 and 10 of the
      amino acid residues are hydrophobic.
<220> FEATURE:
<221> NAME/KEY: misc_feature
<222> LOCATION: (1)..(5)
<223> OTHER INFORMATION: Xaa can be any naturally occurring amino acid
<220> FEATURE:
<221> NAME/KEY: misc_feature
<222> LOCATION: (7)..(16)
<223> OTHER INFORMATION: Xaa can be any naturally occurring amino acid

<400> SEQUENCE: 5

Xaa Xaa Xaa Xaa Xaa Trp Xaa Xaa Xaa Xaa Xaa Xaa Xaa Xaa Xaa Xaa
1               5                   10                  15

<210> SEQ ID NO 6
<211> LENGTH: 16
<212> TYPE: PRT
<213> ORGANISM: Artificial
<220> FEATURE:
<223> OTHER INFORMATION: pAntp Helix 3 Variant; between 6 and 10 of the
      amino acid residues are hydrophobic.
<220> FEATURE:
<221> NAME/KEY: misc_feature
<222> LOCATION: (1)..(5)
<223> OTHER INFORMATION: Xaa can be any naturally occurring amino acid
<220> FEATURE:
<221> NAME/KEY: misc_feature
<222> LOCATION: (7)..(16)
<223> OTHER INFORMATION: Xaa can be any naturally occurring amino acid
```

```
<400> SEQUENCE: 6

Xaa Xaa Xaa Xaa Xaa Trp Xaa Xaa Xaa Xaa Xaa Xaa Xaa Xaa Xaa Xaa
1               5                   10                  15
```

CONJUGATE COMPRISING P21 PROTEIN FOR THE TREATMENT OF CANCER

CROSS-REFERENCE TO RELATED APPLICATION

This application is a continuation of U.S. patent application Ser. No. 11/911,427, filed Jun. 16, 2008, which is the National Stage of International Application Number PCT/GB2006/001407, filed Apr. 18, 2006, both of which are hereby incorporated by reference herein in their entirety, including any figures, tables, nucleic acid sequences, amino acid sequences, or drawings.

FIELD OF THE INVENTION

This invention relates to the P21 protein and conjugates and compositions comprising the P21 protein. These products are particularly useful in the treatment of cancer.

BACKGROUND OF THE INVENTION

Cancer is one of the major causes of human mortality and has been the subject of intensive research. It is well known that almost all malignant tumours result from the transformation of a single cell into an immortal state, where the cell has lost the ability to control proliferation.

Uncontrolled proliferation results from a malfunction in the control of the cell cycle which, in eukarya, is controlled largely by cyclins and cyclin-dependent kinases (CDKs). A complex mechanism of control over the phosphorylation state of the cyclins and CDKs controls whether cyclin/CDK complexes are able to drive the cell into the next phase of the cycle. The importance of the phosphorylation state of cyclin/CDK complexes is reflected by the fact that a large number of cancers involve mutations in the P53 and P21 tumour suppressor proteins, which are key components in the control of cyclin/CDK phosphorylation and complex formation. In particular, P21 blocks cycD/cdk4 complex formation and causes G1 arrest. Reviews detailing the P21 protein and its biological function may be found in O'Reilly M A, Antioxid Redox Signal. 2005 January-February; 7(1-2):108-18 and Liu G & Lozano G, Cancer 25 Cell. 2005 February; 7(2):113-4.

The treatment of cancer usually involves a combination of surgical procedures, radiotherapy and chemotherapy (including immunotherapy). Despite significant advances in cancer therapies in recent years, there remains a constant need for the development of improved therapies. Ideally, a cancer therapy will specifically target and destroy cancerous cells only.

A further problem that needs to be addressed is drug resistance resulting from chemotherapy. The continued administration of a cytotoxic drug can cause a tumour, that was initially sensitive to the drug, to become increasingly drug resistant such that the drug loses its therapeutic efficacy. Methods of improving the sensitivity of cancerous cells to drugs are therefore also required.

BRIEF SUMMARY OF THE INVENTION

This invention is based on the finding that the P21 protein is useful in the treatment of cancer. In particular, a synergistic effect is observed when the P21 protein is administered together with at least one other agent used in cancer therapy.

According to a first aspect of the invention, a conjugate comprises:
  (a) a first region comprising the P21 protein, or a homologue or 10 functional fragment thereof; and
  (b) a second region comprising a translocation factor.

According to a second aspect of the invention, a composition comprises a conjugate comprising a first region comprising the P21 protein, or a homologue or functional fragment thereof, and a second region comprising a translocation factor, in combination with at least one drug.

According to a third aspect of the invention, a conjugate or composition according to the invention may be used as a medicament, particularly for the treatment of cancer.

According to a fourth aspect of the invention, the P21 protein or a homologue or functional fragment thereof may be used as a medicament, particularly for the treatment of cancer.

BRIEF DESCRIPTION OF THE DRAWINGS

The invention is described with reference to the following drawings, wherein.

DETAILED DESCRIPTION OF THE INVENTION

Figure 1:
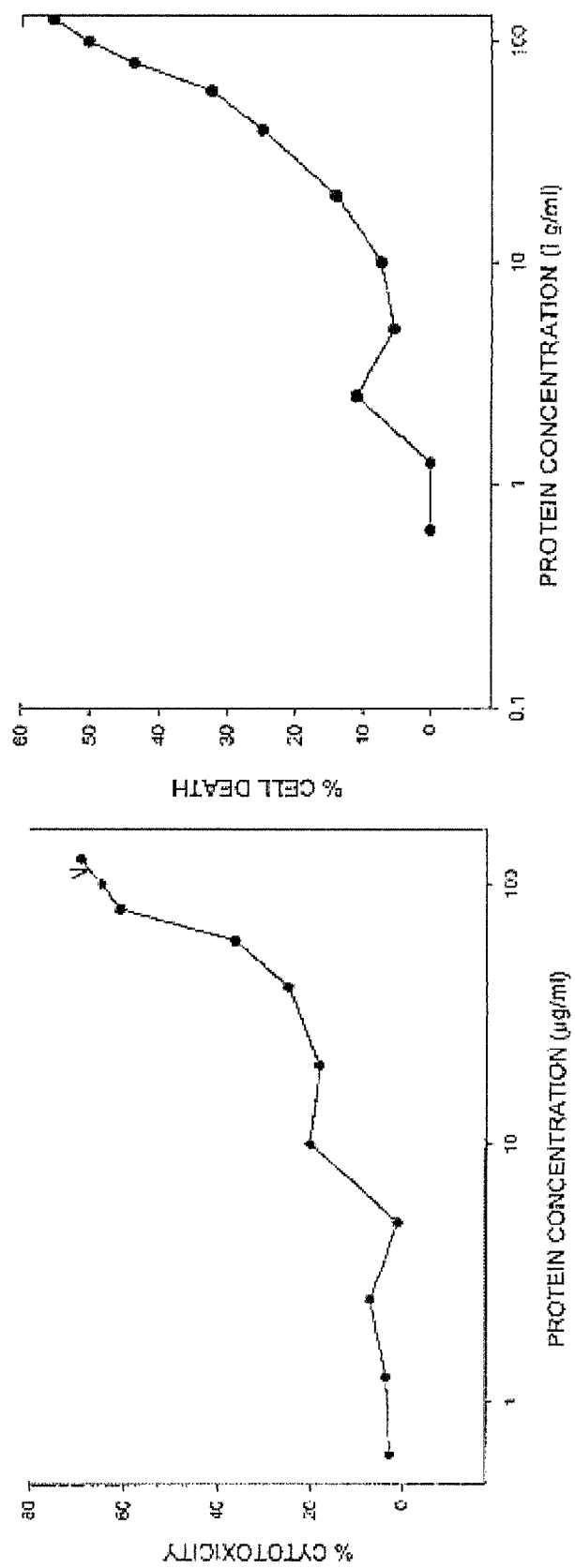
FIG. 1 illustrates the cytotoxicity of antennapedia/P21 fusion protein administered to the ovarian carcinoma cell line SKOV-3 (left) and the osteosarcoma line SAOS-2 (right), which were grown in 96-well ELISA dishes in conditions which resemble the situation in the human body.

The invention utilises the P21 protein as a therapeutic agent. The P21 protein may be used as a therapeutic agent alone or in combination with other therapeutic agents. When used in combination with other therapeutic agents, a surprising synergy is observed. In a preferred embodiment, the P21 protein is attached to a translocation factor, to enable the P21 protein to enter a target cell.

Prior to the present invention, it was not appreciated that P21 could be used extensively in cancer therapy. Most cancers result from mutations in the P53 gene, which is therefore the obvious, and most favoured, target when designing cancer therapeutics. The P21 protein, which functions further down the apoptotic cascade, has not been considered as a therapeutic agent. The present invention bypasses P53 and allows the direct delivery of active P21, for the treatment of cancer.

The administration of P21 and a chemotherapeutic provides a surprising improvement in anti-cancer therapy.

As used herein, the term "protein" refers to a polymer molecule comprising a plurality of amino acid residues linked via the peptide linkage, as will be appreciated by one skilled in the art. Peptides and polypeptides are encompassed with the term "protein".

The human P21 protein is defined herein as SEQ ID NO:1.

```
SEQ ID NO: 1:
SEPAGOVRQN PCGSKACRRL FGPVOSEQLS ROCOALMAGC

IQEARERWNF OFVTETPLEG OFAWERVRGL GLPKLYLPTG

PRRGROELGG GRRPGTSPAL LQGTAEEOHV OLSLSCTLVP

RSGEQAEGSP GGPGOSQGRK RRQTSMTOFY HSKRRLIFSK RKP
```

The annotated human P21 sequence can be found in the SWISSPROT database with the primary accession number P38936 (Entry Name CDN1A_HUMAN). Although the human sequence (SEQ ID NO:1) is preferred, a P21 protein from any species may be used according to the invention, for example the *Mus musculus* protein (SWISSPROT primary accession number P39689) or the *Felis silvestris catus* (Cat) protein (SWISSPROT primary accession number 019002). A polynucleotide encoding a P21 protein is also within the scope of the invention. Functional variants (i.e. homologues) and fragments of the human P21 protein (SEQ ID NO. 1) are also included within the invention. For example, proteins with high levels (e.g. greater than 60%, preferably greater than 70%, more preferably greater than 80% and most preferably greater than 90%, e.g. greater than 95%) of sequence similarity to SEQ ID NO:1 are within the scope of the present invention. The term "similarity" is known in the art. The term refers to a comparison between amino acid sequences, and takes into account not only identical amino acids in corresponding positions, but also functionally similar amino acids in corresponding positions. Similarity between polypeptide sequences therefore indicates functional similarity, in addition to sequence similarity.

Levels of similarity between amino acid sequences can be calculated using known methods. Publicly available computer-based methods for determining similarity include the BLASTP, BLASTN and FASTA programs, the BLASTX program available from NCBI, and the Gap program from Genetics Computer Group, Madison Wis. Levels of similarity referred to herein may, for example, be determined using the Gap program, with a Gap penalty of 12 and a gap length penalty of 4.

Variants or fragments of P21 may be produced using standard recombinant DNA techniques such as site-directed mutagenesis, as will be apparent to the skilled person based on conventional protein technology. Fragments or homologues of the P21 protein should retain the function of the native P21 protein, i.e. should be a "functional" fragment or homologue. The function that must be retained is the ability to act as a tumour-suppressor protein, and block cycD/CDK4 complex formation, and therefore cause G1 arrest of a eukaryotic cell. Tests for cell division and viability are well-known in the art, for example the CellTiter 96® and CytoTox 96® assays available from Promega Corp., Wisconsin USA.

In a preferred embodiment, the P21 protein is associated with a translocation factor, forming a conjugate. As used herein, the term "conjugate" refers to a chimeric molecule formed from a translocation factor and a P21 protein. The conjugate is therefore a hybrid molecule not found together in their natural form. Preferably, the formation of a conjugate does not reduce or otherwise adversely affect the ability of the P21 protein or the translocation factor to function as intended.

As used herein, the term "translocation" refers to the delivery of a protein across a cell membrane. It will be apparent to one skilled in the art that a translocation factor is required to deliver the P21 protein to a target cell. As used herein, the term "translocation factor" refers to any moiety that has the ability to translocate across a cell membrane, i.e. an outer cell membrane. When the P21 protein is associated with the translocation factor in a conjugate, P21 is also translocated across the cell membrane.

The translocation factor will preferably be a protein. A number of proteins with the ability to translocate cell membranes are known in the art, including histone proteins, the herpes simplex virus VP22 protein and HIV tat domain. The tat protein from HIV-type I comprises 86 amino acids encoded by two exons. The first 72 amino acids are encoded by exon 1 and exhibit full trans-activating activity. A cluster of basic amino acid residues in this region are known to be able to translocate across a cell membrane. This cluster, contained within amino acid residues 37-72, is within the scope of the invention. More specifically, amino acids 49-58 are a preferred translocation factor as disclosed by Vives et al., J. Biol. Chem.: 272 (1997); 25: pp. 16010-16017, which is incorporated herein by reference. Amino acids 49-58 of HIV TAT are listed below, as SEQ ID NO:2: SEQ ID NO:2: RKKRRQRRR However, any fragment or homologue of the HIV-type 1 tat protein, that retains the ability to translocate a cell membrane, is within the scope of the invention.

Specific amino acid motifs with the ability to translocate are described in WO03/002598, which is incorporated herein by reference. According to the current invention, it is preferred that the homeodomain of the *Drosophila* antennapedia protein is used as the translocation factor. Functional variants and homologues of the antennapedia homeodomain may also be used, provided that they maintain the ability to translocate. A full description of the antennapedia homeodomain translocation factor is given in WO-A-99/11809, the content of which is incorporated herein by reference. The homeodomain of the Antp gene is shown in SEQ ID NO:3.

```
SEQ ID NO: 3:
RKRGRQTYTR YQTLELEKEF HFNRYLTRRR RIEIAHALCL

TERQIKIWFQ NRRMKWKKEN
```

For the avoidance of doubt, the amino acid sequence of the *Drosophila* antennapedia protein contains a motif of approximately 60 amino acids, known as the homeodomain, which has the ability to function as a translocation factor. The full-length protein, homeodomain or any homologue or fragment (of the protein or homeodomain) that maintains the ability to translocate, may be used as a translocation factor in the present invention. A homologue preferably comprises a region with a high level (e.g. greater than 60%, preferably greater than 70%, more preferably greater than 80% and most preferably greater than 90%, e.g. 95% or more) of sequence similarity to the *Drosophila* antennapedia homeodomain.

Although the *Drosophila* homeodomain and antennapedia full-length protein are preferred, one skilled in the art will realise that functional homologues may originate from any organism. Antennapedia homologues have been found in the majority of multicellular organisms and are well conserved. For example, the human and *drosophila* homeodomains differ by only one conservative amino acid substitution. Homologues produced artificially, for example using site-directed mutagenesis, are also within the scope of the invention. The ability of a naturally-occurring or artificial sequence to translocate the membrane may be tested by routine methods that are well-known in the art.

Variants of the homeodomain which retain the ability to translocate the membrane have been reported in the art and are within the scope of the invention. For example, EP-B-0 485 578 to CNRS discloses homeopeptides comprising the helix 3 sequence of pAntp, and these are incorporated herein by reference.

WO97/12912 also to CNRS discloses the actual sequence of the helix 3 of pAntp, and variants thereof. These also are incorporated herein be reference. In particular, helix 3 is said to have the sequence:

SEQ ID NO:4:
Arg-Gln-Ile-Lys-Ile-Trp-Phe-Gln-Asn-Arg-Arg-Met-

Lys-Trp-Lys-Lys

The variants are said to have the sequence:

SEQ ID NO: 5:
X1-X2-X3-X4-X5-X6-X7-X8-X9-X10-X11-X12-X13-X14-

X15-X16
or

SEQ ID NO: 6:
X16-X15-X14-X13-X12-X11-X10-X9-X8-X7-X6-X5-X4-

X3-X2-X1 wherein each X represents an a-amino acid, with X6 representing tryptophan; said peptide comprising between 6 and 10 hydrophobic amino acids.

Figure 2:
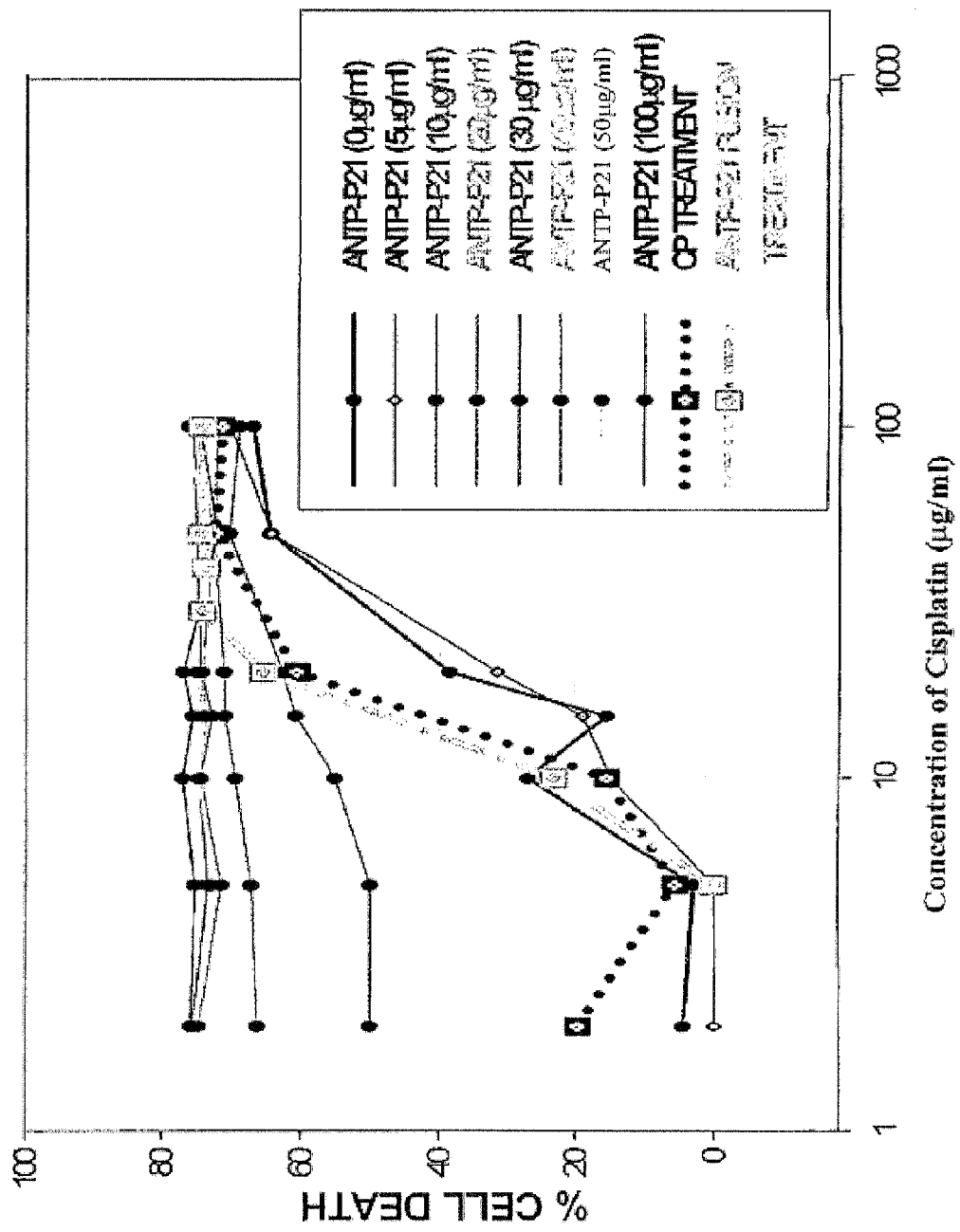
FIG. 2 illustrates the cytotoxicity of the antennapedia/P21 fusion protein and its synergistic effect with cisplatin, and SKOV-3 cells.

Other variants are disclosed in for example, Gehring W (1987) Homeo Boxes in the Study of Development. Science 236:1245-1252 discloses a homeodomain of 62 amino acids, i.e. with glu at position 0 and lys at position 61. Bloch-Gallego E et al. (1993) Antennapedia Homeobox Peptide Enhances Growth and Branching of Embryonic Chicken Motoneurons In Vitro. *The Journal of Cell Biology* 120(2): 485-492 discloses a mutant called pAntp40P2 that was still able to translocate through the motoneuron membrane and to reach the nucleus. In this mutant the leucine and threonine residues in positions 40 and 41 were replaced by two proline residues. Le Roux et al., (1993) Neurotropic activity of the Antennapedia homeodomain depends on its specific DNA-binding properties. *Proc. Natl. Acad. Sci.* 90:9120-9124 discloses two mutants pAntp 50A and pAntp 40P2 as shown in FIG. 2 which retain the ability to translocate through the neuronal membrane. Schutze-Redelmeier et al. (1996) supra disclose that a 16 amino acid C-terminal (third helix) segment has been used to address oligonucleotides and oligopeptides to the cytoplasm and nuclei of cells culture.

All of the references listed above are hereby incorporated wherein by reference. It is preferred that a homeodomain of about 60 residues is used.

It is preferred that the P21 protein and translocation factor are covalently linked. The covalent linkage may be in the form of a chemical linker molecule. More preferably, the P21 protein and translocation factor are produced as a single fusion protein. In the fusion protein, the P21 protein and translocation factor may be in any order. It is preferred that the translocation factor is located at the amino terminal end of the P21 protein. Methods of producing fusion proteins are well known in the art, using standard recombinant nucleic acid procedures, as described in Sambrook et al, Molecular Cloning: A Laboratory Manual (Cold Spring Harbour Laboratory Press), the content of which is incorporated herein by reference. Nucleic acids encoding a fusion protein are within the scope of the invention, as are expression vectors comprising the nucleic acid encoding the fusion protein and at least one promoter region.

The conjugate comprising the P21 protein and a translocation factor can be included in a composition additionally containing at least one drug. Preferably, the drug is used in cancer therapy. In a preferred embodiment, the drug is a chemotherapeutic, for example, cisplatin or taxol. However, other drugs that are used in cancer therapy may also be combined with a conjugate according to the invention, for example anti-inflammatory drugs, antibodies (including monoclonal antibodies), immunomodulating drugs, hormones and hormone antagonists, antibacterials, antifungals and antivirals. Non-limiting examples are given below.

(1) Cytotoxic Drugs/Cytostatics: alkylating agents (eg. cyclophosphamide, melphalan etc.), cytotoxic antibiotics (doxorubicin, epirubicin, bleomycin, mitomycin etc.), antimetabolites (methotrexate, capecitabine, gemcitabine, fluorouracil, vinca alkaloids and etoposide (vinblastine, vincristine etc.), platinum compounds (carboplatin, cisplatin, oxaliplatin), taxanes (paclitaxel, docetaxel etc), topoisomerase I inhibitors (irinotecan, topotecan etc.).

(2) Immune Response Modifiers: antiproliferative immunosuppressants, corticosteroids.

(3) Immunomodulators: interferons, interleukins.

(4) Monoclonals: transtuzumab, rituximab, alemtuzumab.

(5) Antibacterial drugs: penicillins, cephalosporins, cephamycins, tetracyclines, macrolides, aminoglycosides, other antibacterials (chloramphenicol, fusidic acid, vancomycin etc).

(6) Hormones: thyroid hormones, oestrogens, progesterones, androgens, and all their antagonists.

(7) Others: vitamins, non-steroidal anti-inflammatory drugs (e.g. celecoxib, rofecoxib etc), vaccines, antisera, antifungal drugs, antiviral drugs and steroids.

The P21 protein or a homologue or functional fragment thereof, or a conjugate as described above may be used in the treatment of cancer. Preferably, a composition comprising the P21 protein or a conjugate as described above and an additional drug is used in the treatment of cancer.

A pharmaceutical composition containing the active component may be in any suitable form. It is preferred that the P21 protein or conjugate is in a form suitable for transdermal or intravenous administration. Suitable pharmaceutically-acceptable buffers, excipients, diluents etc. may also be present, as well be appreciated by the skilled person. The composition may be in a form intended for administration directly to the diseased tissue or may be in a form that is targeted indirectly to the diseased tissue.

Dosage levels of the order of from about 0.1 mg to about 25 mg per kilogram of body weight per day are useful in the treatment of the above-indicated conditions (about 8 mg to about 2 g per patient per day). For example, the patient may be effectively treated by the administration of from about 0.25 to 12.5 mg of the P21 compound per kilogram of body weight per day (about 20 mg to about 1 mg per patient per day).

The amount of active ingredient that may be combined with the carrier materials to produce a single dosage form will vary depending upon the host treated and the particular mode of administration. Dosage unit forms will generally contain between from about 1 mg to about 500 mg of active ingredient.

It will be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

In addition the P21 compound can be delivered to the site of the disease by mechanical means, or targeted to the site of the disease through the use of systemic targeting technologies such as liposomes (with or without chemical modification that provides them with affinity for the diseased tissue), antibodies, aptamers, lectins, or chemical ligands with affinity for aspects of the diseased tissue that are less abundant or not present on normal tissue.

The invention is further described by the following Examples.

EXAMPLE 1

Bacterial plasmid clones were constructed for the expression of the P21 protein alone or as a fusion to the antennapedia peptide. Expression of the ANTP-P21 fusion (the "fusion protein") was maximal three hours post induction, after which protein purification under denaturing conditions with Guanidinium Hydrochloride and Urea followed. During renaturation and refolding, protein precipitation was observed. This suggested that various buffers needed to be tested. Five buffers were tried; 20 mM Tris-base/0.5 M NaCl/0.1% Tween-20 pH 8 kept the protein in solution.

The production of the fusion protein allowed a cell translocation experiment to be performed, to test the ability of the antennapedia-containing fusion protein to translocate across biological membranes. Two cell lines were used in this experiment, ASPC1 and HeLa (ASPC1—human pancreatic adenocarcinoma, HeLa—human cervical adenocarcinoma). The protein was incubated for 10 and 60 min on cells in various dilutions at 37° C. Translocation of the fusion protein was evident in both cell lines, even after only ten minutes of incubation. P21 protein alone did not appear to translocate across cells. Protein internalisation was even evident after incubation at 4° C., suggesting an energy-independent mechanism of translocation not involving classical endocytosis.

EXAMPLE 2

Expression of the fusion protein was scaled up to purify sufficient material to perform cytotoxicity assays. The protein was dialysed in Guanidinium Hydrochloride solution instead of Tris to prevent it from precipitating. It was expected that, when taken up by cells, endocellular disulphide isomerases and chaperones would result in a functional protein.

The ovarian carcinoma cell line SKOV-3 and the osteosarcoma line SAOS-2 were grown in 96-well ELISA dishes in conditions which resemble the situation in the human body (tissue culture facility).

Fusion protein and P21 alone were given to the cells at 50 mg/ml for 24 and 48 hours. The controls included untreated cells to give the background cell death; cells to which only Guanidinium Hydrochloride was added; and cells which were totally lysed with detergent in order to give 100% cell death. The experiment was terminated at 24 and 48 hours and plates were assessed for apoptotic cell death. The results indicated that the buffer (Guanidinium Hydrochloride) used was itself cytotoxic to the cells after exposure for a prolonged period of time. This background cell death did not allow for any evidence of cytotoxicity due to the fusion protein. Therefore, following refolding the proteins were dialysed in PBS buffer, which is known to be nontoxic to cells. Any precipitated material was removed by centrifugation.

The proteins were then applied to the cell cultures. Significant cell death was observed in two cancer cell lines on administration of the fusion protein as shown in FIG. 1.

Optimization experiments for the conditions of cellular administration were performed. The duration of the administration was tested, as well as the combination of this cytotoxic agent (Antp-P21 fusion) with other agents that are known to kill SKOV-3 cells. An agent used in the experiments was cisplatin. This drug inhibits DNA synthesis by producing intra-strand and inter-strand crosslinks in the DNA. Protein and RNA synthesis are also inhibited to a lesser extent. Results indicated a synergistic effect between the two modes of therapy, and a surprisingly enhanced cytotoxic effect in the presence of both at relatively low concentrations, which should mimic the situation in vivo.

The set of data which demonstrates clearly the killing ability of the Antp-P21 molecule, as well as its synergistic effect with the killing agent cisplatin, is shown in FIG. 2.

The fusion protein was then tested in combination with cisplatin and taxol. Taxol disrupts the dynamic equilibrium within the microtubule system and blocks cells in the late G2 phase and M phase of the cell cycle, inhibiting cell replication. Results indicate a synergistic effect between the three modes of therapy, and an enhanced cytotoxic effect in the presence of the drugs along with the fusion protein at relatively low concentrations.

Figure 3:
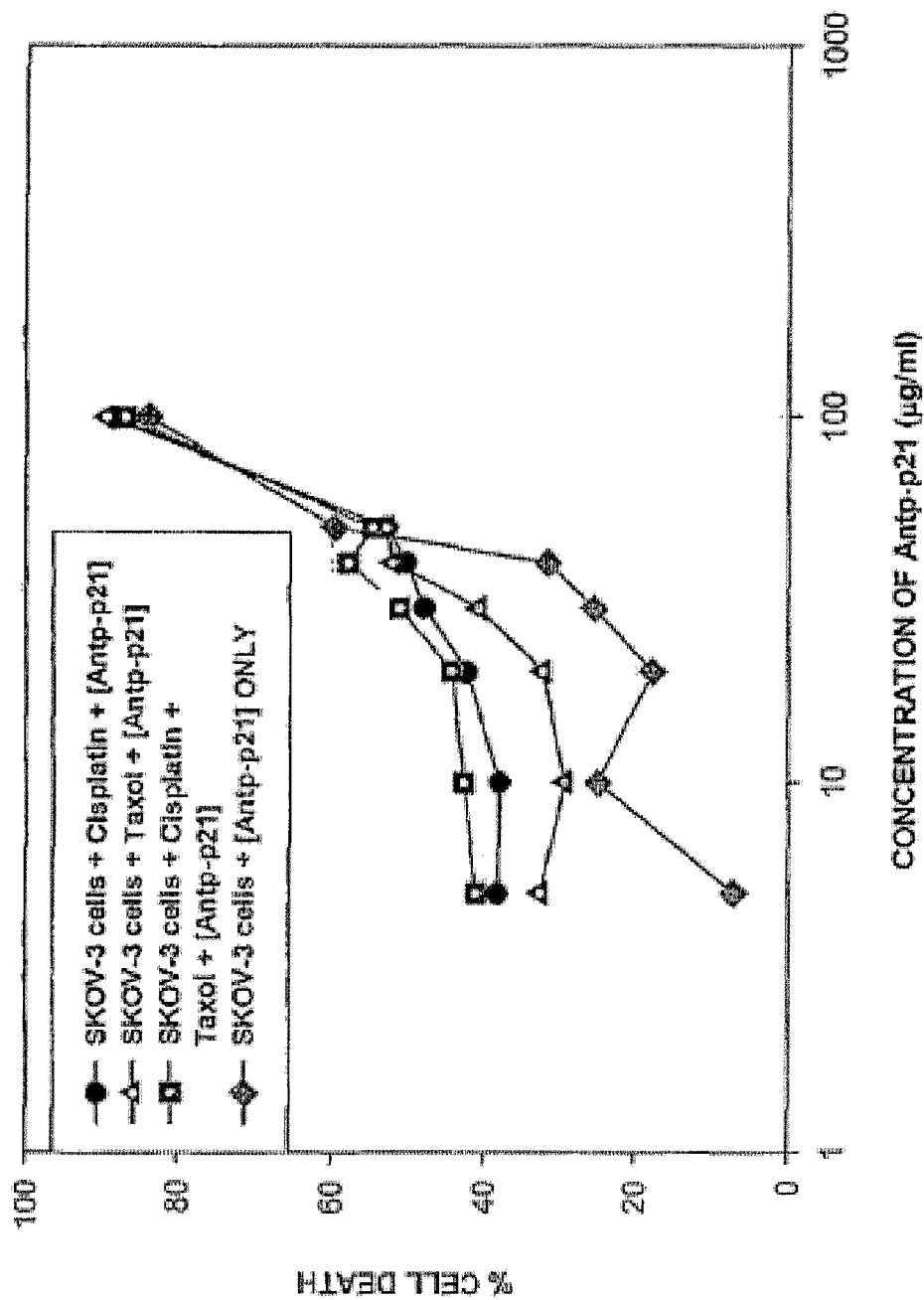
FIG. 3 illustrates the cytotoxicity of the antennapedia/P21 fusion protein in combination with cisplatin and taxol, on SKOV-3 cells, indicating that the antennapedia/P21 fusion, cisplatin and taxol act synergistically when used in combination.

Data which demonstrates the killing ability of the fusion protein together with its synergistic effect with the other killing agents is shown in FIG. 3. The Antp-P21 fusion protein resulted in increased cell death when incubated with the cytotoxic agents cisplatin and taxol. Antp-P21, cisplatin and taxol act synergistically when used in combination.

EXAMPLE 3

Figure 4A:
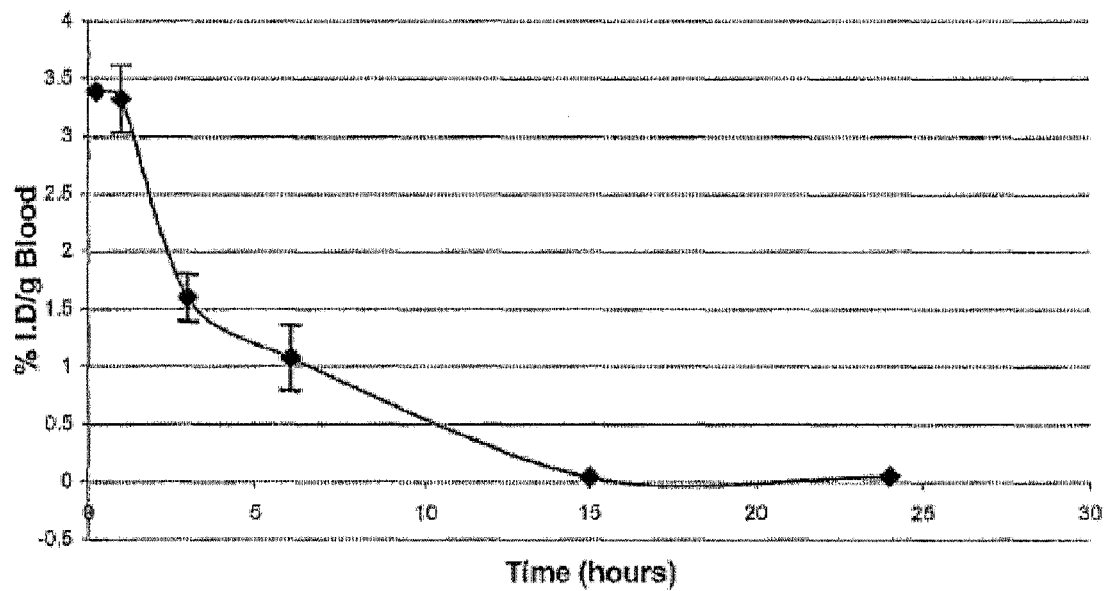
FIG. 4 illustrates the clearance from the blood of purified, radiolabelled antennapedia protein (4A) and antennapedia-P21 fusion protein (4B) in tumour-free mice.

The kinetics and biodistribution of purified, radiolabelled, antennapedia protein (alone) in tumour-free mice was tested. This demonstrates that the protein translocates via the blood to all tissues of the body. A summary of the results is shown in FIG. 4A.

Figure 5A:
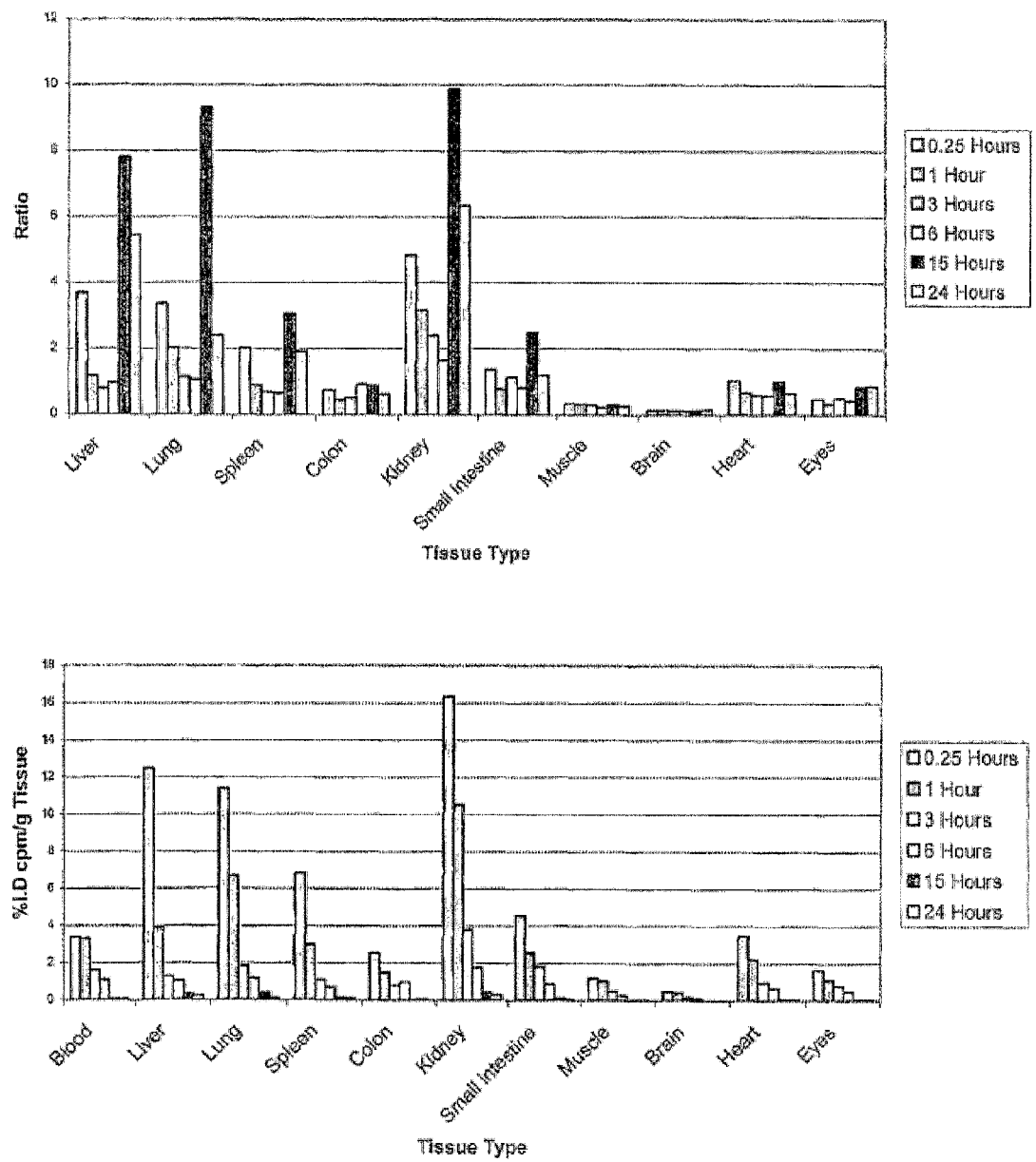
FIG. 5 illustrates the organ-to-blood ratios and the protein accumulation in various organs, for the antennapedia protein (5A) and antennapedia-P21 fusion protein (5B)

The antennapedia protein appeared to have a rapid initial clearance, but it took more than fifteen hours to clear completely from the circulation. This behaviour is expected from positively-charged proteins. This interval should allow sufficient time for it to exit the blood vessels and accumulate in tissues. After dissecting out and counting all organs and tissues of the mice, the organ-to-blood ratios and the protein accumulation in various organs was calculated; as shown in FIG. 5A.

The protein did not have an affinity for any particular type of tissue. It appeared to accumulate in highly vascularised tissues.

Figure 4B:
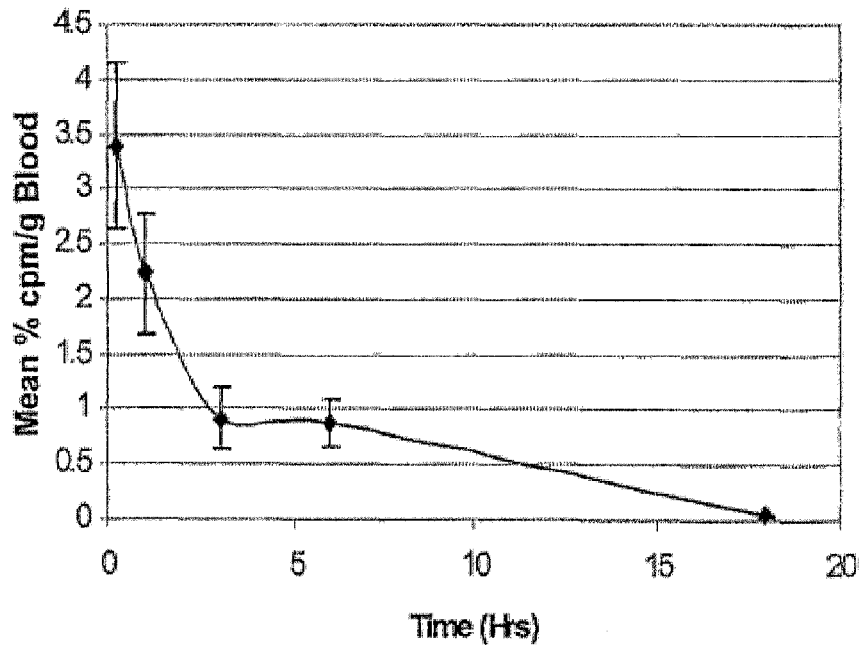
Figure 5B:
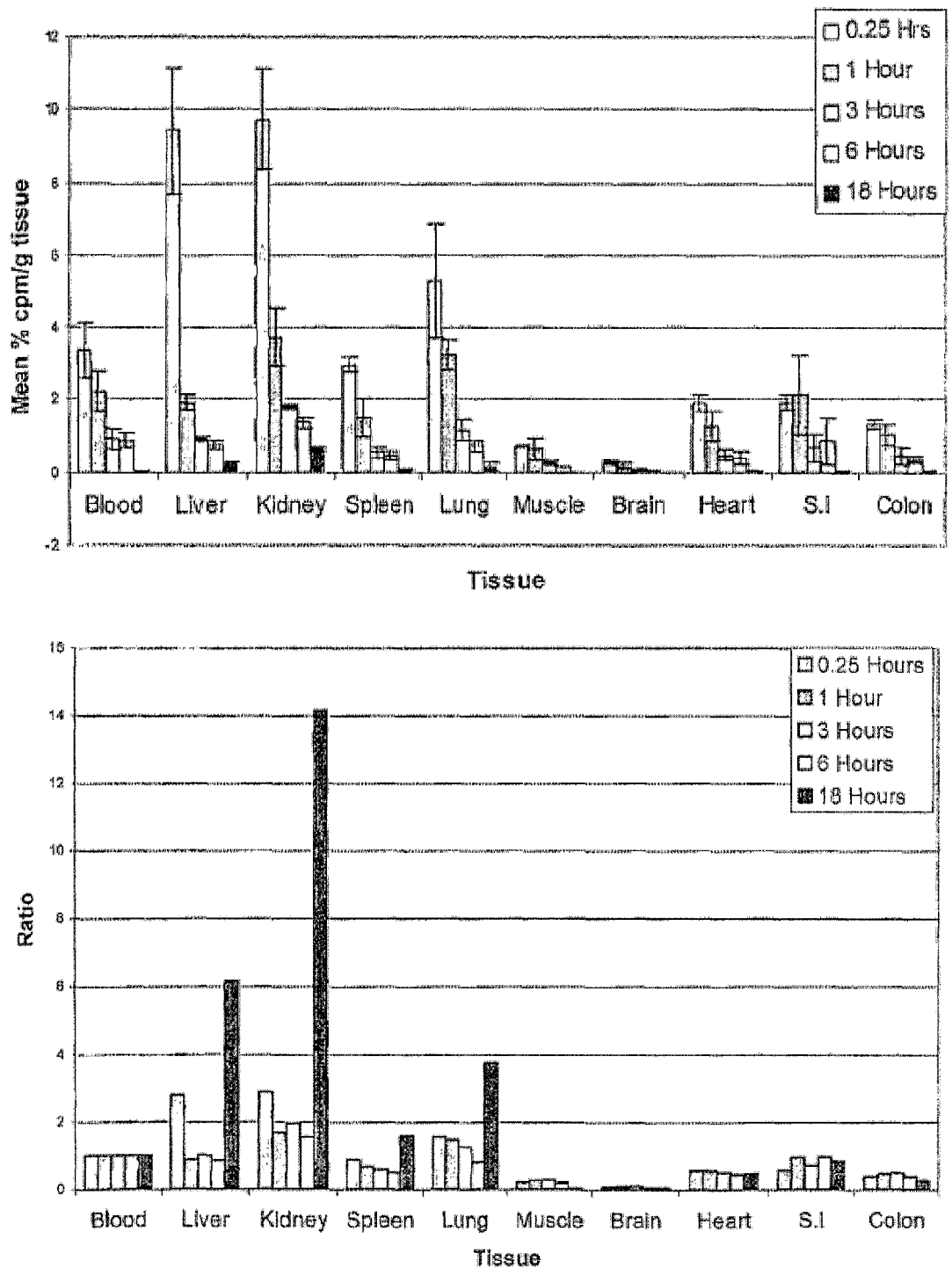

The kinetics and biodistribution of purified, radiolabelled, antennapedia-P21 fusion protein in tumour-free mice were then tested. The results are shown in FIGS. 4B and 5B. The fusion protein appeared to have a rapid initial clearance, but to take more than seventeen hours for it to clear completely from the circulation (FIG. 4B). This behaviour resembled that observed when the antennapedia protein alone was tested, and was expected from positively-charged proteins. This interval was expected to allow sufficient time for it to exit the blood vessels and accumulate in tissues. After dissecting out and counting all organs and tissues of the mice, we were able to calculate the organ-to-blood ratios and to plot the biodistribution of the protein, as illustrated in FIG. 5B.

The fusion protein did not have an affinity for any particular type of tissue, as expected. It appeared to accumulate in highly vascularised tissues. Experiments were performed which allowed us to locate the protein in the tissues by staining with anti-protein antibodies (anti-HIS antibody—Qiagen). These immunohistochemistry studies were performed on frozen tissue sections.

Results showed that the fusion protein accumulated in major organs, as indicated in Table 1, and was found as a full-length molecule. The behaviour of the molecule is likely to remain essentially unaltered in tumour-bearing mice, with the exception of it accumulating in large amounts in the actual tumour.

TABLE 1

| Organ | Staining |
| --- | --- |
| MUSCLE | + |
| COLON | ++ |
| SM. INTEST. | + |
| SPLEEN | ++ |
| LIVER | ++ |
| HEART | + |
| BRAIN | − |
| LUNGS | − |
| KIDNEYS | − |

An experiment was then performed in tumour-bearing animals which indicated the optimal time of protein accumulation in the tumour and therefore the time it takes for the fusion protein to exit the blood circulation and enter the neighboring tissues. This information is desirable when designing experiments which were to involve repeated doses and time interval between each dose.

Radiolabelled fusion protein was administered as a single dose via the tail vein to tumour-bearing mice and tumours examined at various time points. Results demonstrated that the optimal time of tumour localization was three hours after administration. After this period, staining intensity and therefore protein quantity decreased. Results are selectively shown in the following tables:

TABLE 2

T = 15 MIN SKOV-3 tumour-bearing female nude mouse injected with 25 μg of $I^{125}$-labelled Antennapedia-P21 fusion protein via tail vein.
Essentially no staining observed.
% i.d./g tissue 3.2211

TABLE 3

T = 1 hour SKOV-3 tumour-bearing female nude mouse injected with 25 μg of $I^{125}$-labelled Antennapedia-P21 fusion protein via tail vein.
Diffuse staining observed throughout the cells.
% i.d./g tissue 1.7389

TABLE 4

T = 3 hours SKOV-3 tumour-bearing female nude mouse injected with 25 μg of $I^{125}$-labelled Antennapedia-P21 fusion protein via tail vein.
Nuclear localization observed. This is the time point at which maximal staining is observed.
% i.d./g tissue 1.4930

TABLE 5

T = 6 hours SKOV-3 tumour-bearing female nude mouse injected with 25 μg of $I^{125}$-labelled Antennapedia-P21 fusion protein via tail vein.
Staining intensity decreased. Fusion protein is possibly degraded intracellularly.
% i.d./g tissue 1.1064

The maximum tolerated dose which can be safely administered to tumour-bearing mice was then tested. Three different concentrations of the fusion protein was tested, as well as controls, both intravenously and intratumorally. Animals were monitored for signs of distress and toxicity, and measurements of tumour diameter, mice weight and white blood cell count were recorded. The concentration of 2.5 mg/ml of fusion protein was shown to be the highest which can be used without toxicity effects in a repetitive manner and was therefore used in subsequent studies.

Figure 6:
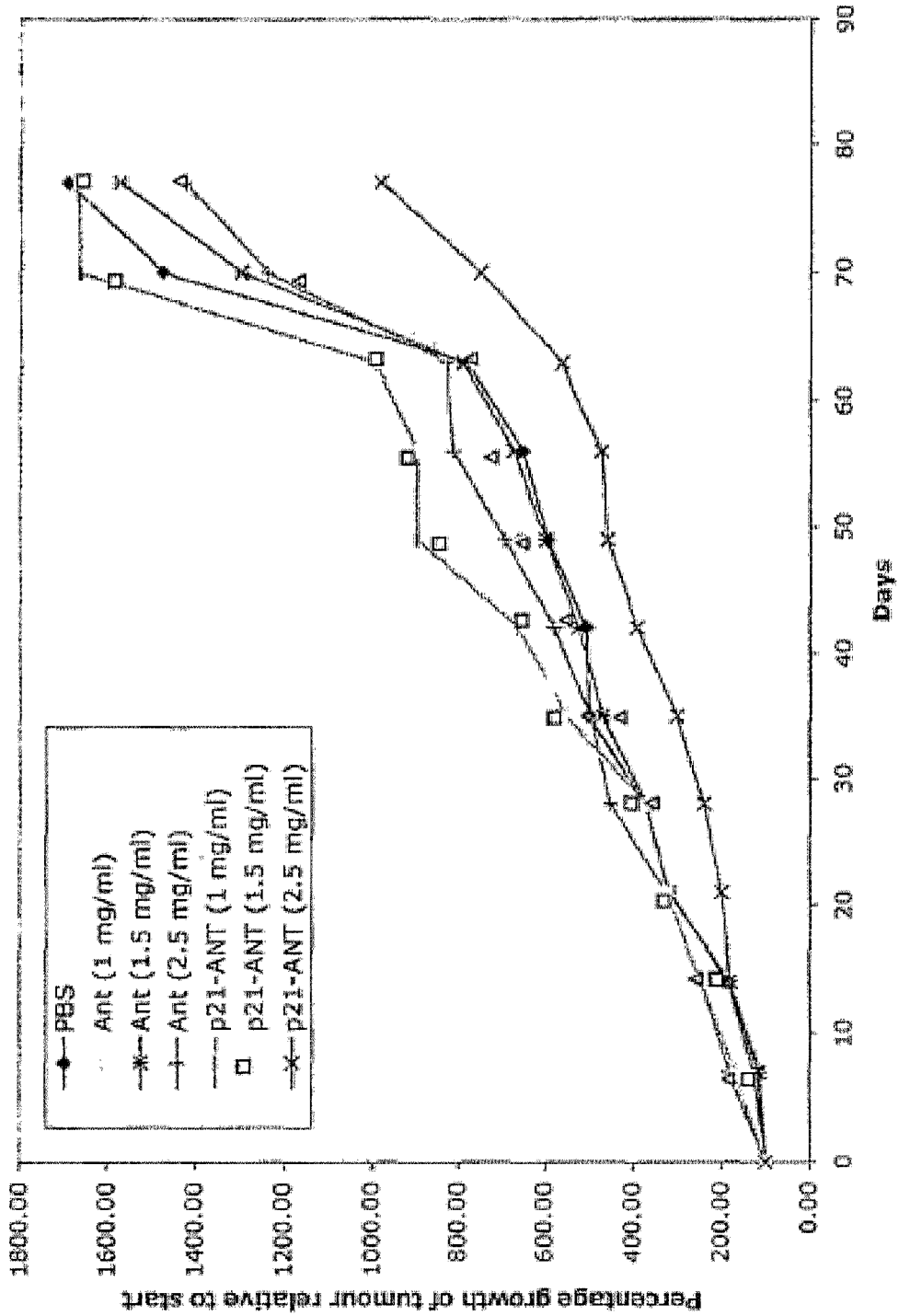
FIG. 6 illustrates the reduction in the growth of tumours using antennapedia/P21 fusion protein.

SKOV3 ovarian adenocarcinoma-bearing xenografts were used. The Antennapedia-P21-treated animals were in large groups of 8 animals, and the experiment included controls such as 8 animals receiving saline solution and 8 animals receiving increasing doses of the Antennapedia protein only. Six injections were performed on a weekly basis. Day zero shown in FIG. 6 is the first day of the injections.

Results indicated that the fusion protein demonstrated maximum tumour delay profile. The concentration of 2.5 mg/ml of the fusion protein, was shown to be the one demonstrating maximum efficacy. When analysing the results further, a survival profile which supported further the mode of action of our therapeutic agent was identified. When grouping animals by tumour size and looking at animals with small starting tumours separately from animals with larger starting tumours, it was noted that the benefit of treatment in small-tumour animals is higher than in animals with larger tumours. Penetration and therapeutic effect of proteins has been shown to be improved in smaller tumours. The rationale behind this is that the interstitial pressure is higher in the core of large tumours and the environment is more difficult for nontargeted molecules to penetrate. Therefore, therapeutic benefit was higher in smaller tumours with lower interstitial pressure.

Figure 7:
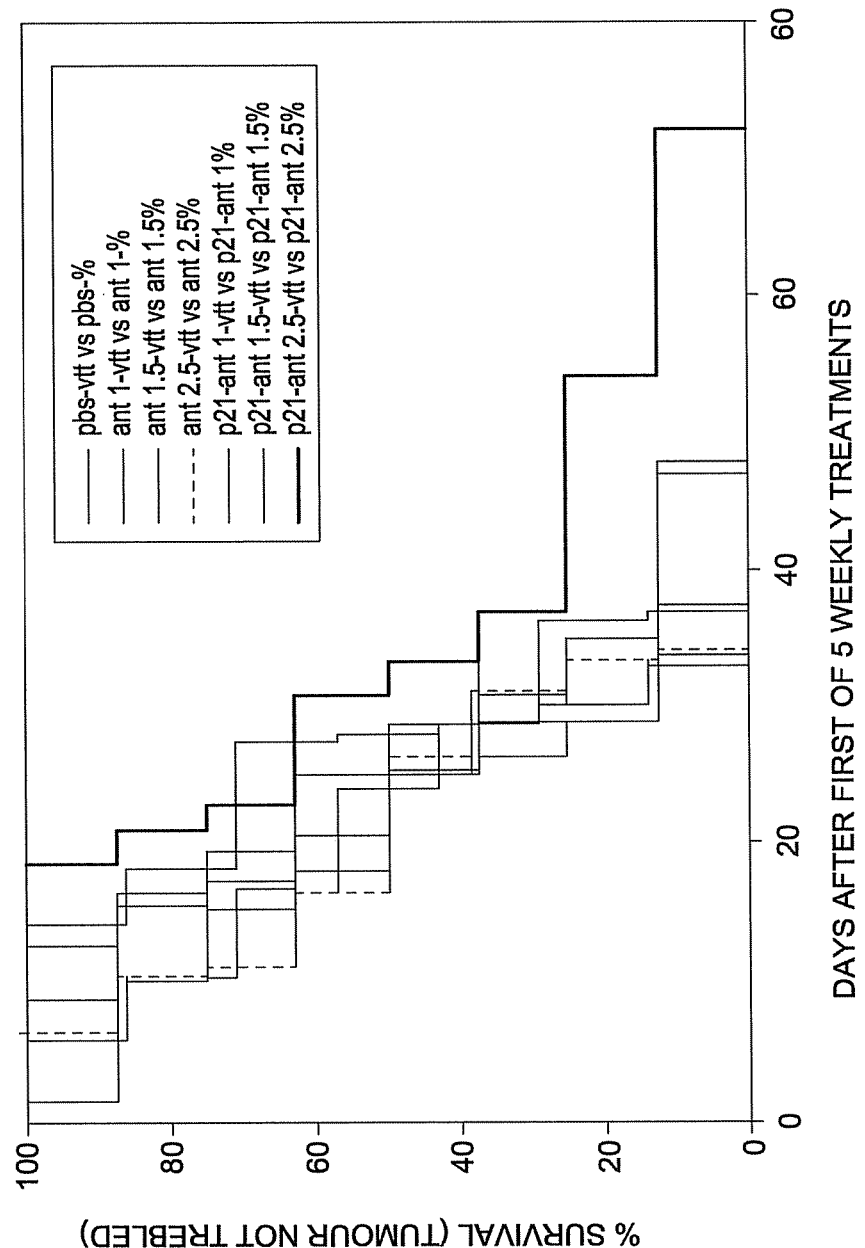
FIG. 7 is a Kaplan-Meier survival curve indicating the survival of mice is greatest when receiving the antennapedia/P21 fusion protein at its highest concentration.

This theory is supported by the Kaplan-Meier data. Analysing all the animals together gives clear survival benefit to the group receiving the fusion protein at its highest concentration as indicated in FIG. 7.

Figure 8:
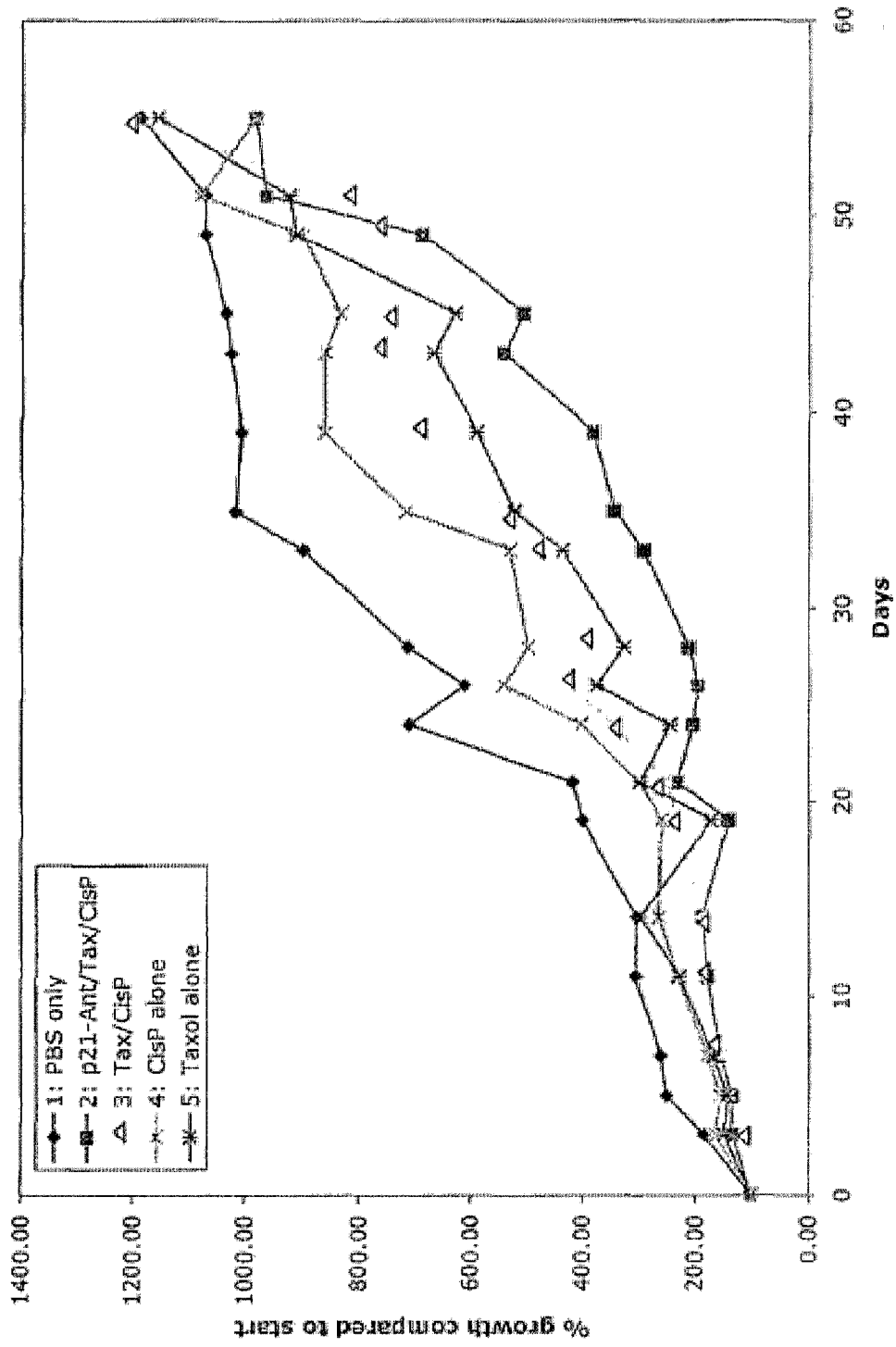
FIG. 8 demonstrates a synergistic effect in vivo when using the antennapedia/P21 fusion protein, taxol and cisplatin.

Conventional chemotherapeutic drugs cisplatin and taxol were added to the therapeutic protocol at standard published doses. In vitro, a positive effect was seen. Results indicated a synergistic effect between the three modes of therapy, and an enhanced tumour growth retardation effect in the presence of the drugs along with the fusion protein at the chosen concentrations, as indicated by FIG. 8.

Figure 9:
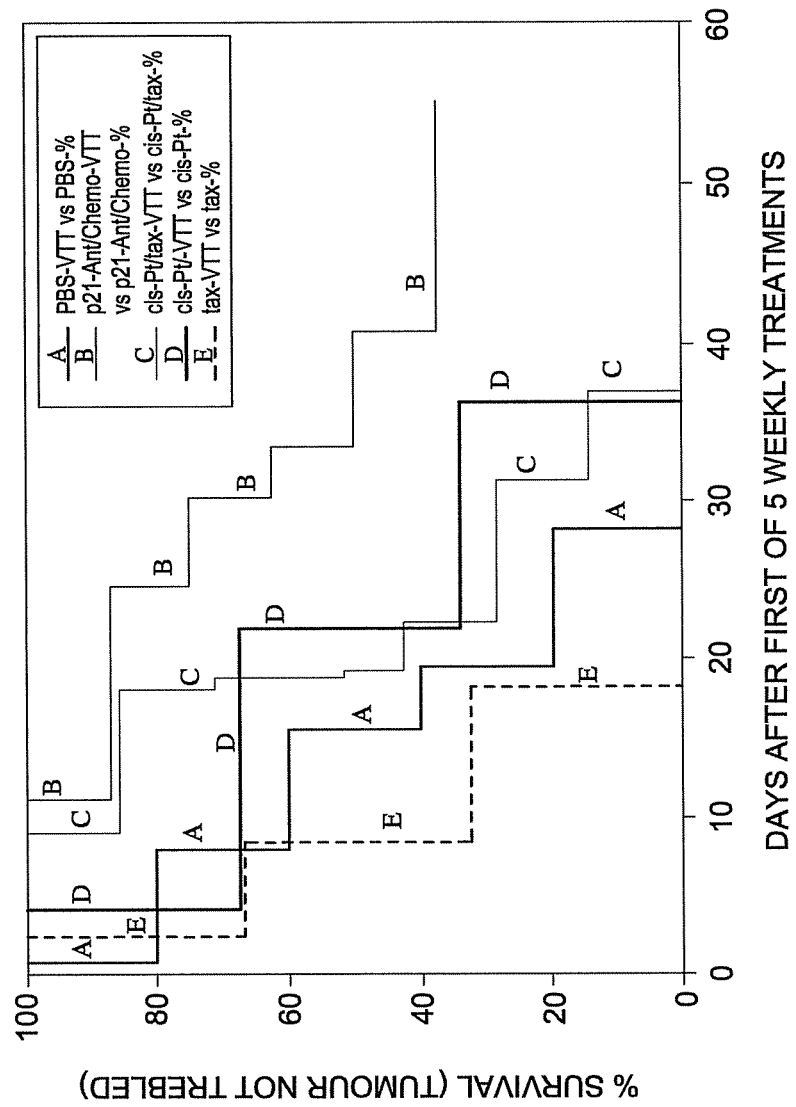
FIG. 9 illustrates the Kaplan-Meier survival curve for mice receiving the antennapedia/P21 fusion protein and chemotherapy. It is clear that the best survival benefit is demonstrated by the animals receiving both the fusion protein and supplementary chemotherapy.

The Kaplan-Meier survival curve for the animals receiving the fusion protein and chemotherapy is given in FIG. 9. It is evident that the best survival benefit was demonstrated by the animals receiving both the fusion protein and supplementary chemotherapy.

Figure 10:
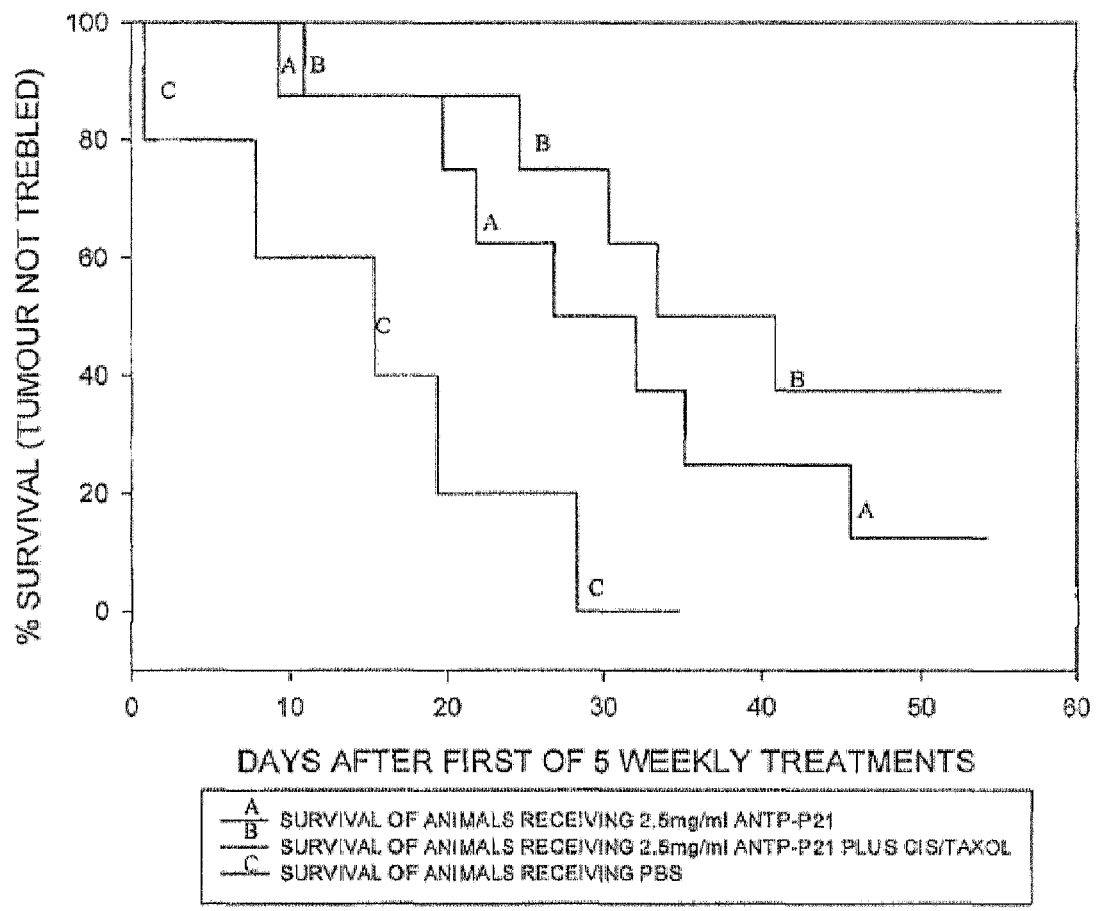
FIG. 10 illustrates the Kaplan-Meier survival curves for mice receiving the antennapedia/P21 fusion and animals also receiving cisplatin and taxol.

When the survival curve of the animals receiving the fusion protein versus the curve of the animals receiving the fusion protein plus complementary chemotherapy were compared, in FIG. 10, it is evident that the addition of chemotherapy increased the percentage of animals alive at all times. This

EXAMPLE 4

Following experiments in SKO-V3 tumours, the fusion protein Antennapedia-P21 was tested in nude mice xenografted with colon carcinoma RKO-E6 cells. These cells contain a stably integrated human papilloma virus (HPV) E6 oncogene under the control of the cytomegalovirus (CMV) promoter. The HPV E6 oncogene causes a decrease in normal p53 levels and functions, to the extent that this line lacks appreciable functional p53.

Lack of p53 blocks downstream p53-mediated transactivation of target genes, such as the Cdk-inhibitor P21. The expression of P21 results in the inhibition of Rb phosphorylation, and, thus, the subsequent expression of E2F-dependent genes is blocked.

The RKO-E6 cell line has been used frequently to investigate the effects of p53 loss on cellular parameter such as p53-mediated transcription and apoptosis. In the experiments described here, it has been used to study the effects of administering P21 to cells, therefore by-passing the need for p53 activation. Apoptosis is measured as tumour cell death and tumour size reduction.

Nude mice were xenografted with RKO-E6 tumours, randomized into four groups and administered one of the following via tail vein injection:
  i. Phosphate-Buffered Solution (once per week for 5 weeks)
  ii. 2.5 mg/ml Antennapedia-P21 Fusion (once per week for 5 weeks)
  iii. 2 mg 5-fluorouracil/1 mg Leucovorin, 0.2 mg Oxaliplatin (once per week for 5 weeks)
  iv. 2.5 mg/ml Antennapedia-P21 Fusion+2 mg 5-fluorouracil/1 mg Leucovorin, 0.2 mg Oxaliplatin (once per week for 5 weeks)

Chemotherapeutic drugs were administered in doses previously documented to cause measurable tumour reductions. Tumour regression was evaluated, which in turn was translated into a survival benefit.

Figure 11:
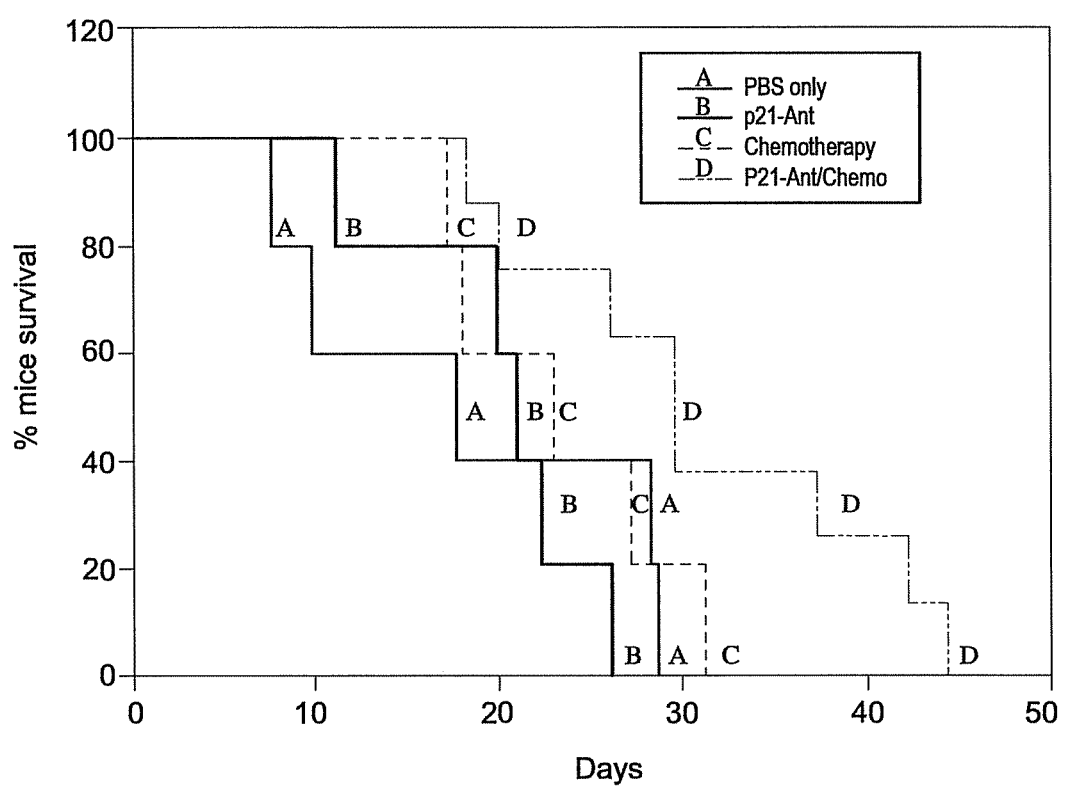
FIG. 11 shows the Kaplan-Meier survival curves for mice receiving the antennapedia/P21 fusion and an additional chemotherapeutic.

Results are shown in FIG. 11. Treatment with PBS, Fusion protein or Chemotherapy alone had little effect on overall survival, with a median survival in the range of 30 days for all these groups. A significant improvement in survival was observed in animals treated with the Fusion in combination to Chemotherapy, with a median survival of 45 days, demonstrating synergistic interactions.

Because a majority of patients who succumb to colorectal cancer do so to secondary systemic metastatic disease, therapeutic strategies which could have an effect on metastatic disease are needed to significantly impact this cancer. The Antennapedia-P21 fusion protein is expected to have such an effect since administration of it has previously been shown to result in its accumulation in various tissues, and because its application has been shown not to be limited by a dose-dependent toxicity.

---

We claim:

1. A method for the treatment of cancer, comprising administering to a subject in need thereof, a conjugate comprising:
   a) a first region consisting of a protein having the amino acid sequence as set forth in SEQ ID NO:1;
   b) a second region comprising the homeodomain of antennapedia; and
   c) a covalent linker.

2. The method according to claim 1, wherein the conjugate is a fusion protein.

3. The method according to claim 1, further comprising administering another agent to the subject, wherein the agent is therapeutic in the treatment of cancer.

4. The method according to claim 3, wherein the agent is a chemotherapeutic drug.

5. The method of claim 1, wherein the cancer is colorectal cancer, ovarian cancer, pancreatic cancer, cervical cancer, or osteocarcinoma.

6. The method of claim 4, wherein the agent is cisplatin or taxol.

* * * * *